(12) United States Patent
Truckai et al.

(10) Patent No.: US 6,663,626 B2
(45) Date of Patent: Dec. 16, 2003

(54) APPARATUSES AND METHODS FOR INTERSTITIAL TISSUE REMOVAL

(75) Inventors: Csaba Truckai, Saratoga, CA (US); Russel M. Sampson, Mountain View, CA (US); Paul K. Hsei, San Jose, CA (US)

(73) Assignee: Novacept, Palo Alto, CA (US)

(*) Notice: Subject to any disclaimer, the term of this patent is extended or adjusted under 35 U.S.C. 154(b) by 0 days.

(21) Appl. No.: 09/930,531

(22) Filed: Aug. 14, 2001

(65) Prior Publication Data

US 2002/0072745 A1 Jun. 13, 2002

Related U.S. Application Data

(62) Division of application No. 09/249,208, filed on Feb. 12, 1999, now Pat. No. 6,296,639.
(60) Provisional application No. 60/092,572, filed on Jul. 13, 1998.

(51) Int. Cl.[7] .............................................. A61B 18/18
(52) U.S. Cl. .......................................... 606/41; 606/45
(58) Field of Search ..................... 606/41, 42, 45–52

(56) References Cited

U.S. PATENT DOCUMENTS

| | | | |
|---|---|---|---|
| 2,022,065 A | 11/1935 | Wappler | |
| 3,850,175 A | 11/1974 | Iglesias | |
| 3,942,530 A | 3/1976 | Northeved | |
| 4,108,182 A | 8/1978 | Hartman et al. | |
| 4,660,571 A | 4/1987 | Hess et al. | |
| 4,986,825 A | 1/1991 | Bays et al. | |
| 5,030,201 A | 7/1991 | Palestrant | |
| 5,100,423 A | 3/1992 | Fearnot | |
| 5,125,928 A | * 6/1992 | Parins et al. .................. | 606/48 |
| 5,192,280 A | * 3/1993 | Parins .......................... | 606/48 |
| 5,201,729 A | 4/1993 | Hertzmann et al. | |
| 5,217,458 A | * 6/1993 | Parins .......................... | 606/48 |
| 5,269,780 A | * 12/1993 | Roos ............................. | 606/42 |
| 5,318,576 A | 6/1994 | Plassche, Jr. et al. | |
| 5,415,656 A | 5/1995 | Tihon et al. | |
| 5,437,665 A | 8/1995 | Munro | |
| 5,441,499 A | 8/1995 | Fritzsch | |
| 5,456,684 A | * 10/1995 | Schmidt et al. ............... | 606/41 |
| 5,471,982 A | 12/1995 | Edwards et al. | |
| 5,524,180 A | 6/1996 | Wang et al. | |
| 5,527,326 A | 6/1996 | Hermann et al. | |
| 5,554,163 A | 9/1996 | Shturman | |
| 5,556,408 A | 9/1996 | Farhat | |

(List continued on next page.)

FOREIGN PATENT DOCUMENTS

| | | |
|---|---|---|
| DE | 3339322 A1 | 5/1984 |
| WO | WO 98/33445 A1 | 8/1998 |
| WO | WO 99/04704 A2 | 2/1999 |

OTHER PUBLICATIONS

T. Lorentzen et al. "The loop electrode: a new device for US–guided interstitial tissue ablation using radiofrequency electrosurgery—an animal study," (1996) *Min. Invas. Ther. & Allied. Technol.* 5:511–516.

Primary Examiner—Michael Peffley
(74) Attorney, Agent, or Firm—Townsend and Townsend and Crew LLP

(57) ABSTRACT

Apparatuses and methods for removing solid tissue from beneath a tissue surface are described. The methods rely on positioning an energy conductive element at a target site beneath the tissue surface and energizing the element so that it can vaporize tissue. The element is then moved in a pattern which provides the desired tissue removal geometry, such as spherical, ovoid, or cylindrical. Usually, the shaft is moved, typically rotated or reciprocated, and the energy conductive element is moved relative to the shaft, typically by pivoting a rigid element or bowing a flexible element.

15 Claims, 10 Drawing Sheets

U.S. PATENT DOCUMENTS

| | | | |
|---|---|---|---|
| 5,569,164 A | * 10/1996 | Lurz | 600/158 |
| 5,578,007 A | 11/1996 | Imran | |
| 5,658,280 A | 8/1997 | Issa | |
| 5,702,390 A | 12/1997 | Austin et al. | |
| 5,715,817 A | 2/1998 | Stevens-Wright et al. | |
| 5,728,143 A | 3/1998 | Gough et al. | |
| 5,730,704 A | 3/1998 | Avitall | |
| 5,735,847 A | 4/1998 | Gough et al. | |
| 5,738,683 A | 4/1998 | Osypka | |
| 5,782,828 A | 7/1998 | Chen et al. | |
| 5,810,806 A | * 9/1998 | Ritchart et al. | 606/45 |
| 5,827,276 A | 10/1998 | LeVeen et al. | |
| 5,871,469 A | 2/1999 | Eggers et al. | |
| 5,888,198 A | 3/1999 | Eggers et al. | |
| 5,899,912 A | 5/1999 | Eaves, III | |
| 5,902,272 A | 5/1999 | Eggers et al. | |
| 5,902,300 A | 5/1999 | Hahnen et al. | |
| 5,904,679 A | 5/1999 | Clayman | |
| 5,913,857 A | 6/1999 | Ritchart et al. | |
| 5,935,125 A | 8/1999 | Zupkas | |
| 5,938,661 A | 8/1999 | Hahnen | |
| 5,944,715 A | 8/1999 | Goble et al. | |
| 5,944,716 A | 8/1999 | Hektner | |
| 5,980,504 A | 11/1999 | Sharkey et al. | |
| 6,007,512 A | 12/1999 | Hooven | |
| 6,032,673 A | 3/2000 | Savage et al. | |
| 6,050,995 A | 4/2000 | Durgin | |
| 6,068,603 A | 5/2000 | Suzuki | |
| 6,280,450 B1 | 8/2001 | McGuckin, Jr. | |
| 2001/0047169 A1 | 11/2001 | McGuckin, Jr. et al. | |
| 2002/0019640 A1 | 2/2002 | McGuckin, Jr. et al. | |
| 2002/0022850 A1 | 2/2002 | McGuckin, Jr. et al. | |

* cited by examiner

APPARATUSES AND METHODS FOR INTERSTITIAL TISSUE REMOVAL

This patent application is a division of application Ser. No. 09/249,208, filed on Feb. 12, 1999, now U.S. Pat. No. 6,296,639 which also claims priority from provisional Application No. 60/092,572 filed on Jul. 13, 1998, under 35 U.S.C. §119(e)(1), the full disclosure of which is incorporated herein by reference.

BACKGROUND OF THE INVENTION

1. Field of the Invention

The present invention relates generally to medical devices, kits, and methods. More particularly, the present invention relates to apparatuses and methods for removing tissue from tissue regions beneath a tissue surface.

The removal of diseased and other tissues is the basis for many surgical procedures and is accomplished in many different ways. Most commonly, the target tissue is excised using a cutting blade, such as a scalpel, in open surgical procedures. Typically, the cutting blade is advanced into a tissue through an exposed tissue surface, and the target tissue is simply cut out and removed. While very effective for tissue removal at or near an exposed tissue surface, this approach is less effective for tissue removal from sites spaced below the closest exposed tissue surface.

For removal of target tissue below a tissue surface, a surgeon can simply cut down to the level of the target tissue and cut out and remove the tissue at that level. The need to cut down through "non-target" tissue is, however, disadvantageous in several respects. First, surgically cutting through the overlying healthy tissue can create a much bigger incision than is necessary for simply removing the target tissue. Moreover, the need to penetrate through relatively thick layers of overlying tissue can complicate identification of the target region, often requiring that larger volumes of tissue be removed to assure to complete removal. Additionally, the ability to cut down into internal organs during minimally invasive endoscopic procedures is significantly more limited than in open surgical procedures.

Surgical instruments for removing tissue beneath a tissue surface have been developed. For example, instruments employing specialized cutting blades for chopping or "morcellating" tissue into small pieces and aspirating the resulting debris have been developed. While such instruments are at least theoretically capable of being manipulated to remove a defined volume of tissue beneath a tissue surface, their performance suffers in various ways. Most importantly, tissue morcellation can result in significant bleeding which is difficult to staunch. Thus, these techniques would not be useful in highly vascularized tissues, such as many muscle and organ tissues. Even when combined with electrosurgical coagulation, such tissue morcellation devices are probably not useful for the removal of large tissue volumes beneath a tissue surface where bleeding control is problematic.

For all of these reasons, it would be desirable to provide improved apparatuses and methods for tissue removal beneath tissue surfaces. In particular, the devices and methods should be suitable for use in minimally invasive procedures, such as procedures where the devices are introduced through a port and viewed under endoscopic viewing. The methods and devices should further allow access to a target tissue region with minimum disruption and damage to the overlying "non-target" tissue. Additionally, it would be desirable to provide tissue removal regions with a simplified approach for removing the debris resulting from the tissue removal. It would be particularly desirable to provide such tissue removal methods and devices which result in minimum or easily controlled bleeding at the tissue removal site. Such methods and apparatuses should still further provide for removal of controlled volumes, even relatively large volumes of at least 0.5 cm$^3$, preferably at least 50 cm$^3$, and still more preferably at least 500 cm$^3$, or more. The methods and apparatuses should also be useful on a wide variety of tissue types and for a wide variety of specific procedures. At least some of these objectives will be met by the invention described hereinafter.

2. Description of the Background Art

A loop electrode for radiofrequency electrosurgical excision of a tissue volume in solid tissue is described in Lorentzen et al. (1996) Min. Invas. Ther. & Allied Tecnol. 5:511–516.

Three-dimensional electrode arrays for deployment in solid tissue followed by the application of radiofrequency energy to necrose tissue volumes are described in U.S. Pat. Nos. 5,827,276; 5,735,847; and 5,728,143.

Atherectomy catheters having radially expansible blade structures intended for rotational stenotic excision in blood vessels are described in U.S. Pat. Nos. 5,556,408; 5,554,163; 5,527,326; 5,318,576; 5,100,423; and 5,030,201. In particular, U.S. Pat. No. 5,554,163, describes a catheter having a flexible "cutting" element that may be radially deployed from the catheter body. U.S. Pat. No. 5,100,423, describes a cutting structure comprising a plurality of helically-shaped cutting wires that can be connected to an electrosurgical power supply to effect cutting of obstructing matter in a blood vessel. The following patents describe other electrosurgical instruments: U.S. Pat. Nos. 2,022,065; 4,660,571; 5,217,458; 5,578,007; 5,702,390; 5,715,817; 5,730,704; 5,738,683; and 5,782,828.

SUMMARY OF THE INVENTION

The present invention provides improved methods, devices, and kits for removing tissue from internal target sites disposed beneath a tissue surface. The present invention can provide a number of advantages when compared to prior tissue removal techniques, including minimizing disruption of the tissue overlying the target site, i.e., between the tissue surface and an outer periphery of the target volume which is to be removed. In the preferred examples described below, access through the overlying tissue can be achieved with a single percutaneous or transcutaneous tissue tract sufficient to accommodate a single shaft of the apparatus. In addition to minimizing disruption of overlying tissue, the present invention can significantly reduce bleeding at the target site after tissue removal. In particular, by employing electrocautery as part of the tissue excision process, bleeding of the surrounding tissues can be substantially staunched. Other advantages provided by the present invention include the ability to remove relatively large tissue volumes, typically, at least 0.5 cm$^3$, often at least 50 cm$^3$, and sometimes as large as 500 cm$^3$, or larger. While the present invention is particularly suited for removing large volumes. The tissue removal can be effected in many tissue types, including those specifically set forth below, and tissue debris remaining after removal can be transported from the site, typically through the single access tract described above, usually by aspirating vapors and cellular debris which are produced as the tissue excision and vaporization stages occur. In addition or as an alternative to vapor aspiration, the tissue void which is being created may optionally be flushed with a suitable liquid or gas, preferably an electrically non-conductive liquid, such as sorbitol. Further optionally, the flushing medium may carry medications or other biologically active substances, such as antibiotics, pain killers, hemostatic agents, and the like. Such flushing may occur concurrently with the cutting, during brief periods when cutting is ceased, and/or after all cutting has been completed.

The present invention is suitable for removing defined volumes of tissue from a variety of different tissue types, including breast tissue, liver tissue, kidney tissue, prostate tissue, lung, uterine, and the like. Thus, the tissue surface may be on the patient's skin, e.g., in the case of breast tissue removal, or the tissue surface may be located subcutaneously, e.g., in the case of internal body organs. In the former case, access to the target site may be achieved transcutaneously or subcutaneously, where the removal device penetrates directly through the skin. In the latter case, a secondary procedure is needed to access the tissue surface of the internal body organ. The secondary procedure may be an open surgical procedure where the overlying skin and body structures are surgically opened. Alternatively, the secondary procedure may itself be minimally invasive where small incisions or ports are used to introduce the devices of the present invention together with any necessary or useful auxiliary devices for performing the tissue removal. Typically, such minimally invasive surgeries will be performed under endoscopic visualization where the treating physician views the procedure on a video screen. As a still further alternative, access to internal body organs may be achieved intraluminally, preferably endoscopically. Typically, such intraluminal, endoscopic access will be obtained through body lumens having natural orifices, such as the esophagus, colon, uterus, fallopian tubes, sinuses, uterus, ureter, and urethra. Such access will typically be achieved using a flexible catheter which can provide a platform for advancing the energy conductive elements, as described in more detail below.

The depth of the target site will depend on the nature of the tissue and the nature of the disease or other condition being treated. Typically, the closest periphery of the target site will be located between the adjacent or available tissue surface by distance in the range from 0.5 cm to 15 cm, usually from 5 cm to 7 cm. The volume of tissue to be removed will typically be in the range from 0.5 cm$^3$ to 500 cm$^3$, typically being from 5 cm$^3$ to 300 cm$^3$. As described in more detail below, the geometry or shape of the removal volume, i.e., the void left in tissue following tissue removal, will generally be spherical, ovoid, cylindrical, or other shape characterized by at least one axis of symmetry. The axis of symmetry will usually arise because of the manner in which the tissue removal devices are used, as described in more detail below.

In a first aspect, methods according to the present invention comprise positioning an energy conductive element at a target site in tissue beneath a tissue surface. The energy conductive element is energized and moved through successive tissue layers, where the element is energized with sufficient energy to vaporize tissue in said successive layers. Such sequential removal of successive layers of tissues will produce a desired removal volume, typically having the geometries and sizes set forth above.

In a second aspect, methods according to the present invention comprise providing an instrument having a shaft and a repositionable energy conductive element on the shaft. The element is advanced through the tissue surface to a target site in solid tissue, where the element is in a low profile configuration (e.g., radially collapsed into the shaft) and the proximal end of the shaft remains outside of the solid tissue to permit manipulation. The shaft is moved relative to the tissue surface and the element repositioned relative to the shaft while the element is being energized with sufficient energy to remove tissue. The combined movements of the shaft and the element relative to the shaft cause the element to pass through successive tissue layers at or near the target site and to vaporize said layers to produce the desired removal volume.

Usually, the methods for removing tissue as described above will further comprise imaging the solid tissue and positioning the energy conductive element based on the image. The imaging may be any type of conventional, two-dimensional or three-dimensional medical imaging, including fluoroscopic imaging, ultrasonic imaging, magnetic resonance imaging, computer-assisted tomographic imaging, optical imaging, and the like. Positioning of the energy conductive device may be entirely manual, where the user may view the image of the target site either in real time, as a pre-operative image only, or a combination of real time and pre-operative images. Alternatively, the energy conductive device may be automatically positioned based directly or indirectly on the image using robotic or other automatic positioning equipment. Optionally, such automatic positioning equipment can be programmed based on a pre-operative or real time image of the target region.

The methods of the present invention will preferably further comprise collecting vapors and cellular debris produced by the tissue vaporization and removing those vapors through the overlying tissue and the tissue surface. Usually, vapor removal will comprise aspirating the vapors from the site or volume of tissue removal as the vapors are being produced. Usually, the vapors will be aspirated through a tissue tract between the tissue surface and the target site, more typically being through a lumen in the shaft of the device used for removing the tissue.

The energy conductive element is moved through a pattern of successive tissue layers which, in the aggregate, will form the desired tissue removal volume. The energy conductive element may be moved in any manner, typically being moved by manipulation of the shaft upon which it is mounted. For example, the energy conductive element may be moved relative to the shaft while the shaft itself is moved so that the combined motions of the element and the shaft define the desired removal geometry. Alternatively, the energy conductive element could be moved on the shaft while the shaft remains stationary. In the latter case, a servo or other drive mechanism could be provided within the shaft to move the energy conductive element through its desired pattern.

The shaft will usually be rotated and/or axially reciprocated in order move the energy conductive element through tissue along or about one axis. In turn, the energy conductive element may be pivoted, bowed, or otherwise moved or deflected relative to the shaft to provide further axes or dimensions of the removal volume. In a first exemplary removal method, a shaft having a rigid energy conductive member is introduced to an internal tissue target site with the element lying coaxial to the shaft. The shaft is then rotated and the element pivoted to provide a spherical or partial spherical tissue removal geometry. In a second exemplary embodiment, the energy conductive element comprises one or more flexible elements which may be bowed to form a series of arcuate tissue removal paths as the shaft is rotated. Other approaches include disposing a lateral energy conductive element beneath tissue and simultaneously rotating and reciprocating the support shaft so that a cylindrical removal volume is formed, with the length of the cylinder determined by the length of reciprocation. Other combinations of motion between the shaft and energy conductive element may also be utilized.

The type of energy transmitted or provided through the energy conductive element will preferably provide for heating of the tissue. For example, high frequency energy, such as radiofrequency or microwave energy, may be delivered in a monopolar or bipolar manner to vaporize the tissue. Typically, the radiofrequency energy will be applied with a cutting waveform at a frequency in the range from 100 kHz to 2 MHz, and a current in the range from 1 mA to 50 A, 0.5 mA to 10 A, depending on surface contact area and tissue type. Alternatively, energizing can comprise directly heating the element, typically to a temperature in the range from 100° C. to 300° C., usually 600° C. to 2000° C. Heating is preferably achieved using optical energy, e.g., laser energy, delivered through a fiberoptic element within the energy conductive element. Alternatively, heating can be achieved using an electrical resistance heater which comprises or is disposed within the energy conductive element.

The present invention further provides apparatus for removing tissue. In a first instance, a tissue ablation device comprises a shaft having a proximal end, a distal end, and a lumen therethrough. At least one flexible energy conductive element is disposed near the distal end of the shaft, and a means for bowing the element between a substantially linear profile (where the element lies directly over the shaft) and a series of arcuate profiles spaced progressively further from the shaft is provided. The bowing means will typically include a mechanism for axially advancing a proximal end of the flexible energy conductive element. By preventing or limiting axial movement of a distal end of the flexible energy conductive element, the element will be caused to bow radially outwardly in the desired arcuate configuration. Alternatively, a proximal end of the flexible energy conductive element may be fixed or limited relative to the shaft and a rod or other device for proximally retracting a distal end of the energy conductive element provided. It would further be possible to simultaneously draw both ends of the element together. Other mechanisms, such as expandable cages, parallel linkages, shape heat memory drivers, or the like, may also be provided for bowing the element radially outwardly. The tissue ablation device will further comprise an aspiration connector coupled to the lumen for aspirating vapors produced at the distal end. A power supply connector is further provided to permit electrical coupling of the energy conductive element to a desired power supply.

The shaft of such devices may be substantially rigid, typically having a diameter in the range from 0.5 mm to 20 mm, typically 2 mm to 7 mm, and a length in the range from 2 cm to 50 cm, usually 5 cm to 25 cm. The devices will also typically have a handle secured at or near the proximal end of the shaft, and at least one of the aspiration and power supply connectors will usually be disposed on the handle. Optionally, a motor may be provided in the handle or separate from the handle to help drive the device. For example, the motor could be connected to rotate and/or reciprocate the shaft relative to the handle in order to drive the device in a desired manner. Alternatively or additionally, the motor could be connected to bow the flexible energy conductive element in a controlled manner. In the exemplary embodiments, however, all motions of both the shaft and the energy conductive element will be manual.

The shaft of such devices may also be flexible, typically in the form of a catheter having a diameter in the range from 0.5 mm to 10 mm, and a length in the range from 25 cm to 250 cm. Usually, when used for access to natural body lumens, such as the colon, uterus, esophagus, fallopian tubes, sinuses, uterus, ureter, and the urethra, the shafts will be introduced through or as part of an endoscope. The cutting elements for performing the tissue removal will then be deployed from or near the distal end of the catheter. Typically, the cutting elements will be deployed laterally from the catheter and a stylet or other introducer will be utilized to permit subcutaneous introduction as required by the present invention. In other cases, the devices may be introduced intravascularly, typically through the femoral or other veins, to target organs, such as liver, kidney, prostate, lung, and uterus. The cutting elements can then be deployed from the catheters through the blood vessel wall into the target organ.

The energy conductive elements may be configured to provide for any of the energy delivery modes set forth above. In particular, energy conductive elements may comprise electrodes suitable for the delivery of high frequency electrical energy, typically radiofrequency energy having the particular frequencies and other characteristics set forth above. Alternatively, the energy conductive elements may be configured to provide for direct heating of the elements themselves, usually comprising either an optical fiber for delivering light energy or comprising an electrical resistance heater together with the necessary wiring to connect the resistance heater to a suitable power source.

The flexible energy conductive elements may take a wide variety of forms. A first exemplary form will be a simple elastic or super elastic metal wire, typically having a diameter in the range from 0.1 mm to 5 mm, preferably from 0.5 mm to 2 mm. The wire may be formed from any suitable material, including stainless steel, nickel titanium alloy, tungsten, or the like. The wire may be composed of single material or may be a composite material, e.g., where a portion of the wire is selected for high electrical conductivity while another portion of the wire selected for elastic or other properties. The electrically conductive elements may also be in the form of ribbons, i.e., having a width substantially greater than its thickness. Such ribbon structures will have greater mechanical rigidity when they are radially expanded through their narrow dimension. Often times, different types of energy conductive elements may be combined in a single device. In an exemplary device, a pair of wire elements are disposed on opposite sides of the shaft with a pair of ribbon elements offset by 90°. Each of the four elements is coupled to the other so that they open and close (be "bowed" and relaxed) synchronously. Usually, such structures will be formed for bipolar operation, where the ribbon elements will have a much greater surface area than the wire elements so that the ribbons connect as a dispersible electrode, i.e., an electrode where minimum cutting takes place. In such cases, the ribbon electrode can also serve to act as a surface coagulation electrode to help control bleeding. In some instances, it will be desired that the wire cutting electrodes be advanced slightly radially ahead of the ribbon electrodes. Such a design allows the ribbons to open under a spring force to "automatically" expand as the wire electrodes remove successive layers of tissue.

A second exemplary tissue ablation device comprises a shaft having a proximal end, a distal end, and lumen therethrough. A substantially rigid energy conductive element is pivotally attached to the shaft near its distal end. The device further includes a means for causing the element to pivot, such as a push wire, pull wire, rack and pinion driver, gear driver, or the like. The device will further include aspiration and power supply connectors, both as generally described above.

The nature of the shaft and the types of energy conductive elements which may be deployed are all similar to corresponding aspects of the first embodiment of the tissue ablation device described above. The nature of the pivotally connected energy conductive element will, however, differ. The pivotally attached energy conductive element will usually be straight, typically being in the form of a cylindrical pin having a length in the range from 1 mm to 75 mm, and a width or diameter in the range from 0.5 mm to 5 mm. A preferred geometry includes a circular or flat cross-section. The rigid element may be pivotally attached near its middle, near one end thereof, or anywhere else along its length. In an illustration example, the element is pivotally attached near its middle in order to effect a spherical tissue removal volume as the device is rotated and the pin pivoted through 90° or more, as described in detail below.

The present invention still further provides kits comprising a device having an energy conductive element which is connectable to a power supply and which provides energy sufficient to vaporize successive layers of tissue as the element is moved therethrough. The device may have any of the configurations described above. The kit will further comprise instructions for use setting forth a method as in any of the methods described above. Typically, at least the device will be present in a sterile package, and the instructions for use may printed on a portion of the package or may be on a separate instruction sheet accompanying the package. Suitable packages include pouches, trays, boxes, tubes, or the like. Suitable sterilization techniques include gamma radiation, ethylene oxide treatment, or the like.

DESCRIPTION OF THE SPECIFIC EMBODIMENTS

Figure 1:
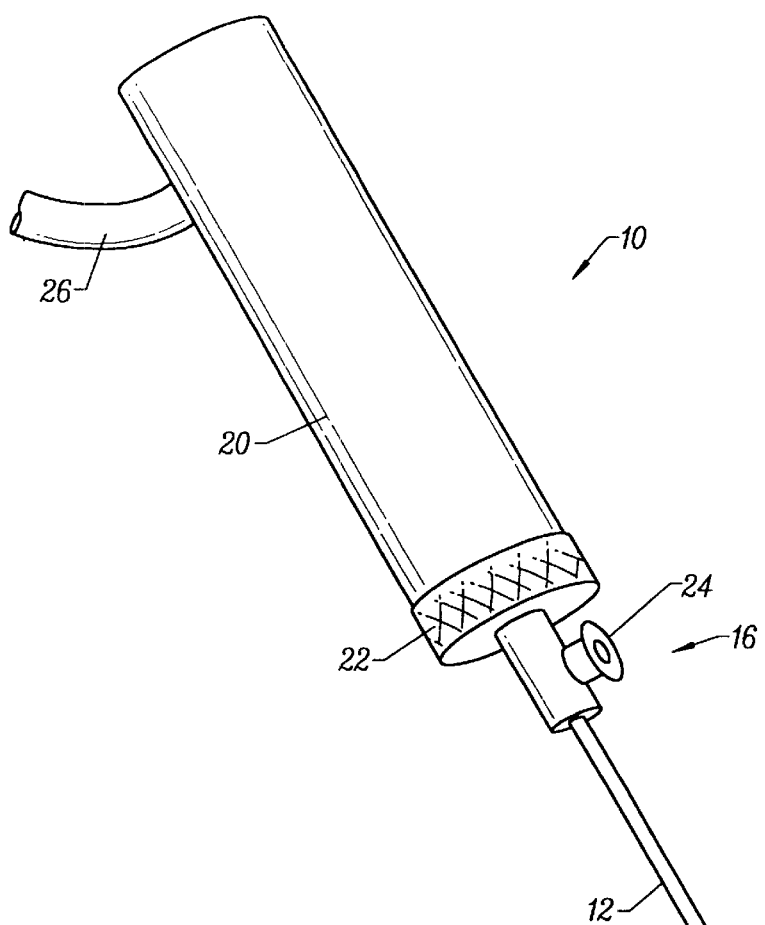
FIG. 1 illustrates a perspective view of a first apparatus constructed in accordance with the principles of the present invention.

Referring now to FIG. 1, a tissue ablation device 10 comprises a shaft 12 having a distal end 14 and a proximal end 16. An energy conductive element 18, typically a rigid cylindrical electrode or pin, is pivotally attached at point 19 to the distal end of the shaft 12. Handle 20 is connected to the proximal end 16 of the shaft, and a lead screw 22 is provided near a distal end of the handle to cause pivoting of the element 18 and/or rotation of the shaft 12 relative to the handle. Usually, the lead screw 20 is coupled to the pivoting element 18 through a push/pull wire 21 which passes through the shaft 12 and emerges near the distal end 14 thereof. The push/pull wire 21 is shown to be attached near an outer end of the element 18, it could of course be connected much more closely to the pivot pin. Moreover, numerous other pivoting mechanisms could be provided, as described above.

Figure 2A:
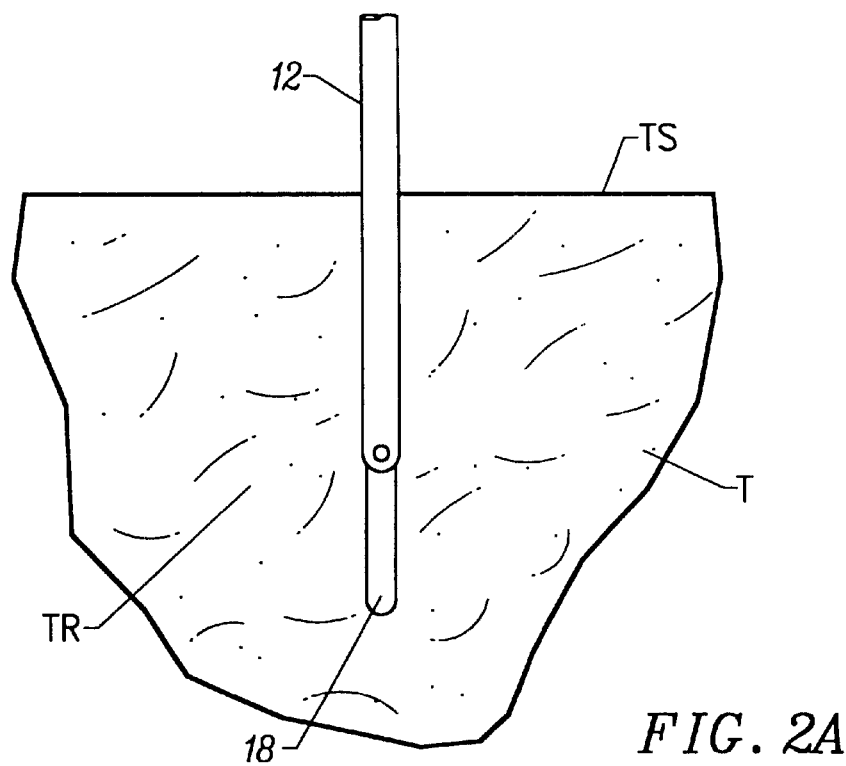
FIGS. 2A–2D illustrate use of the apparatus of FIG. 1 in performing a method according to the principles of the present invention.

Referring now to FIGS. 2A–2D, use of the tissue ablation and device 10 to vaporize and remove a target region TR of tissue T beneath a tissue surface TS will be described. Initially, the device 10 is connected to an electrosurgical power supply through connector cable 26. The electrosurgical power supply, typically operating at a frequency in the range from 100 kHz to 2 MHz, with conventional sinusoidal or non-sinusoidal waveforms. Preferably, the power supply will be set to provide a cutting waveform at a power level within the ranges set forth previously. Suitable power supplies are available from commercial suppliers, such as Valleylabs, Aspen, Bovie, and Birtcher. After connection, the energy conductive element 18 will be axially aligned with the shaft and penetrated beneath the tissue surface, as illustrated in FIG. 2A. Optionally, the radiofrequency current may be applied through the element 18 to facilitate the initial penetration. With the embodiment of FIG. 1, the device will usually be operated in a monopolar fashion with one pole of the power supply being connected to the element 18 and a second pole being connected to a dispersive electrode which is attached to the exterior patient's skin, typically in the lower back area. In some instances, the device of FIG. 1 can be provided with bipolar elements 18, e.g., with a pair of conductive stripes formed on the element, in order to permit bipolar operation, i.e., where both poles of the electrosurgical power supply are connected to the stripes on the element. Moreover, while the cutting current will usually be applied with a cutting waveform during tissue removal, at other times during the process it may be desirable to coagulate the tissue by applying a coagulation waveform. This can be done at the end of the cutting procedure, when some instances may be performed in alternative cycles with the cutting process in order to inhibit excessive bleeding during the operation.

Figure 2B:
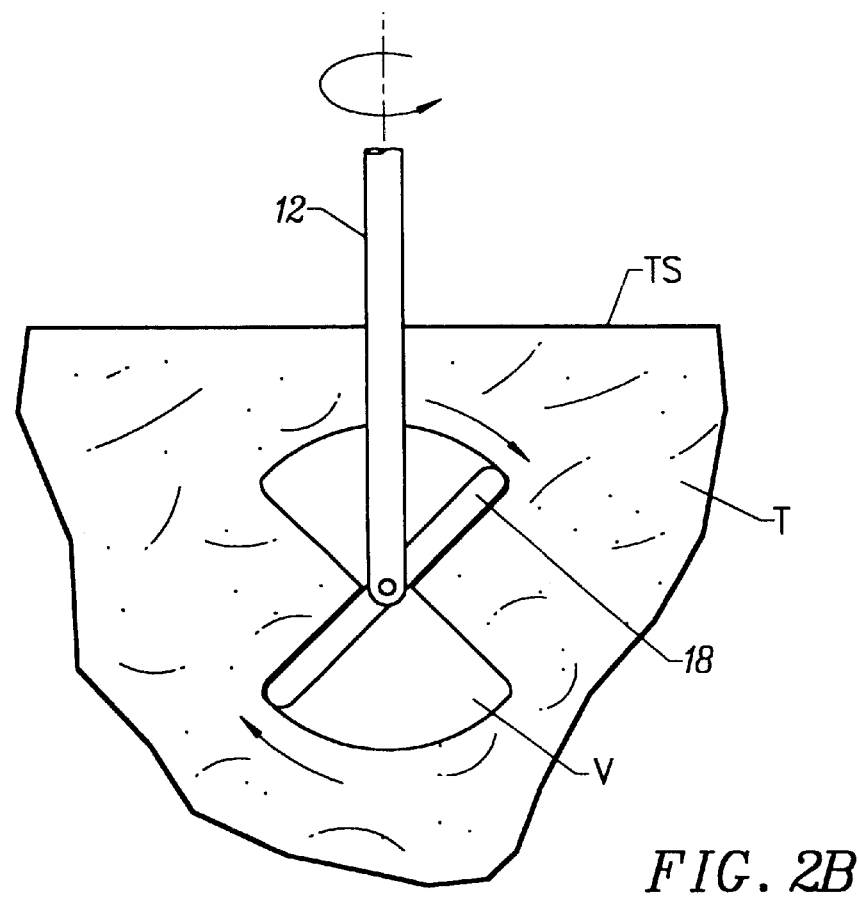
Figure 2C:
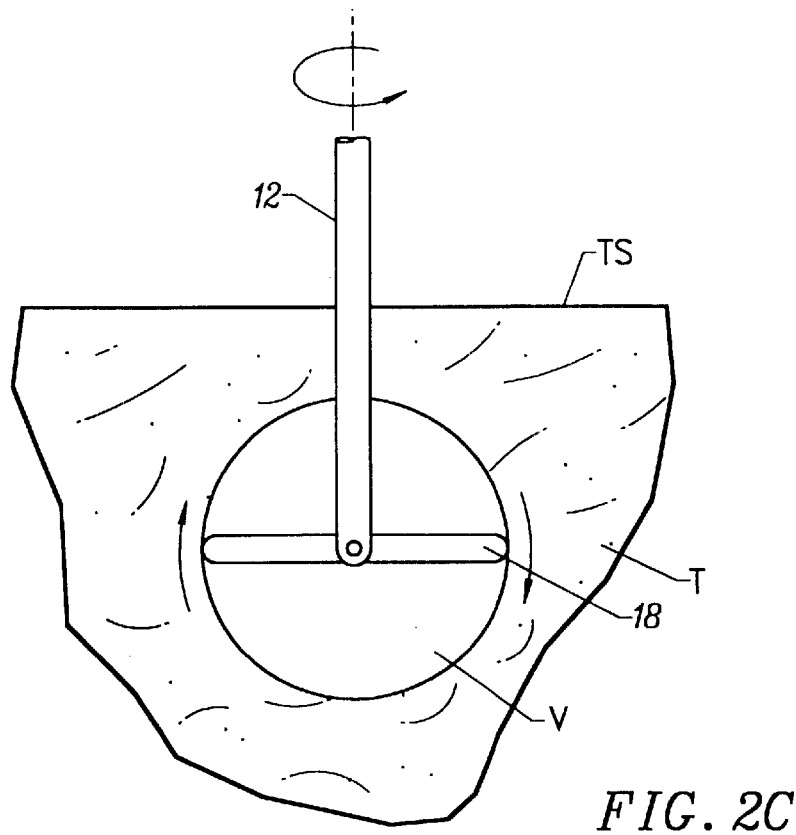
Figure 2D:
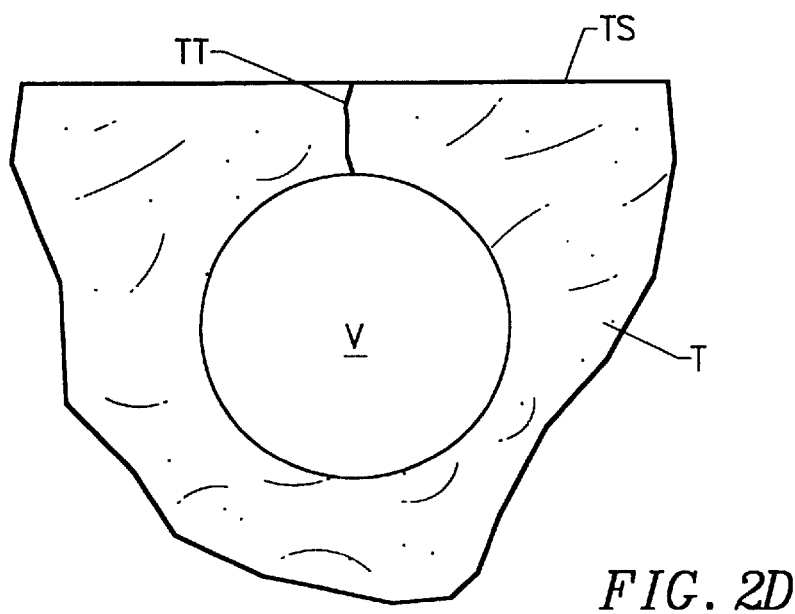

After the device 10 is initially positioned, as shown in FIG. 2A, the shaft 12 will be rotated and the element 18 pivoted in the direction of the arrows shown in FIG. 2B. The result is a void or cavity V being formed in the solid tissue with an initial geometry comprising a pair of cones joined at their apices. As the shaft 12 continues to be rotated and the energy conductive element 18 continues to be pivoted in the direction of the arrows, the two cones will grow until they join into a generally spherical void V, as shown in FIG. 2C. After the spherical void is completed, the element 18 may be returned to its coaxial configuration, and the shaft 12 and element 18 is withdrawn, leaving the void V intact at the end of a closed tissue tract TT, as illustrated in FIG. 2D.

The use of radio or other high frequency electrical energy is preferred for forming the tissue void as just described. The radiofrequency energy will not only vaporize tissue, permitting the resulting vapors to be withdrawn through the lumen of the shaft 12 (typically by connecting aspiration port 24 to a suitable vacuum source), but also cauterize the inner surface of the void as it is being formed. Such cauterization, in turn, limits or controls bleeding as the tissue is being removed. After the removal is complete, it may be desirable to introduce collagen, gelatin, autologous tissue, or other biologically compatible tissue fillers into the void region to inhibit tissue collapse, further control bleeding, deliver drugs (which may be incorporated into such matrices), or the like.

Alternatively, after a tissue void has been created, the void can simply be collapsed in order to "debulk" a tissue region. For example, for the treatment of benign prostate hyperplasia, it may desirable to remove a small volume of tissue and thereafter collapse the tissue to release pressure on the urethra. Optionally, a tissue glue, sealant, or other material, may be introduced after the tissue void has been collapsed in order to maintain the collapsed configuration.

Figures 3A, 3B:
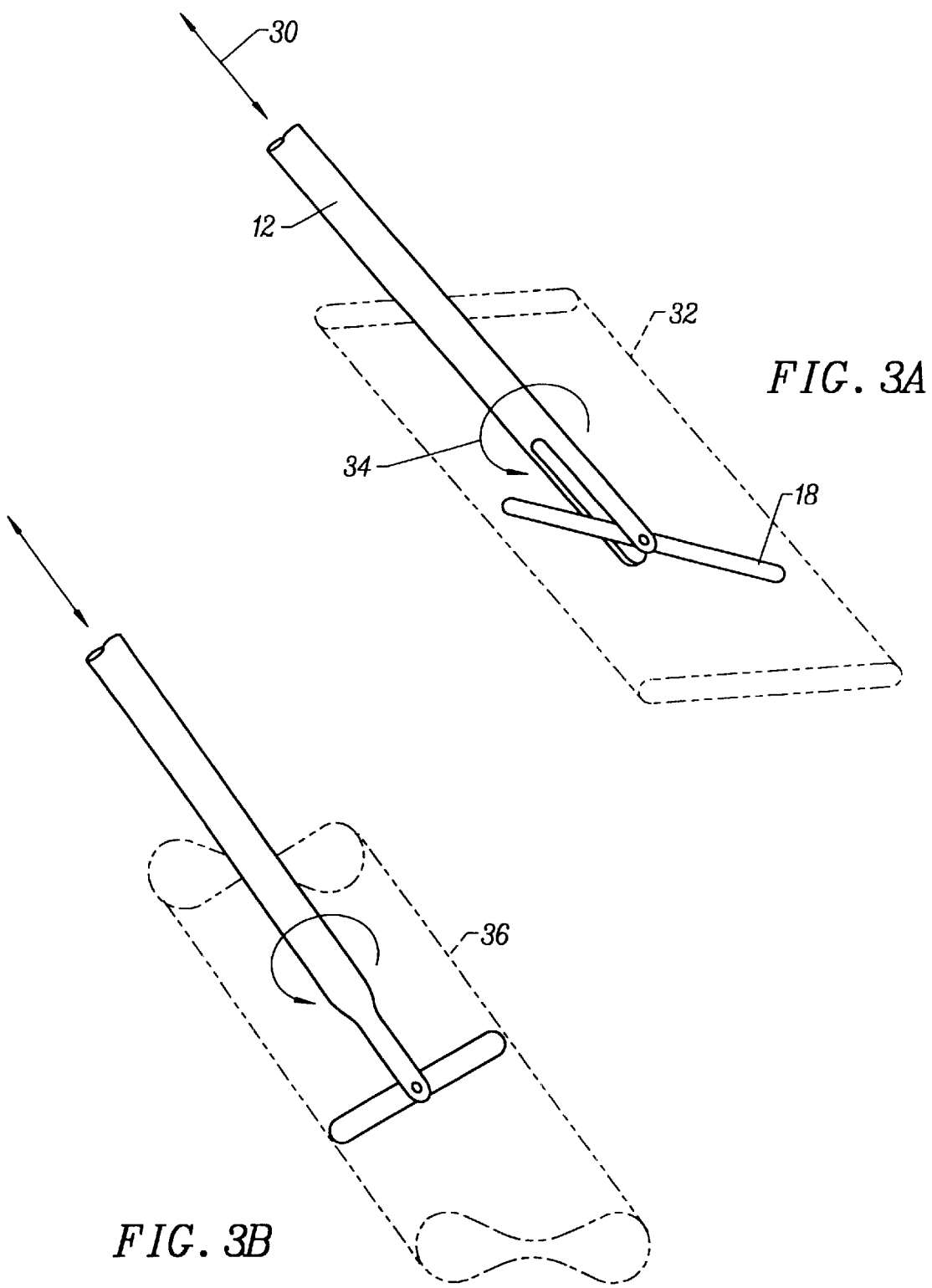
FIGS. 3A and 3B illustrate use of the apparatus in FIG. 1 in performing an alternative embodiment of the method of the present invention.

Referring now to FIGS. 3A and 3B, the device 10 could be utilized in other specific treatment protocols. For example, as illustrated in FIG. 3A, the device 10 may be introduced so that energy conductive element 18 on shaft 12 is initially pivoted at 90° so that it lies transversely with respect to the axis of shaft 12. Shaft 12 may then be axially reciprocated in the direction of arrow 30. Initially, a relatively flat layer of tissue 32, as shown in broken line, will be removed with the reciprocation. By then slowly rotating the shaft 12, as shown by arrow 34, and continuing to reciprocate the shaft in the direction of arrow 30, the removed tissue volume will grow to have an hourglass-shaped cross-section, as shown in broken line pattern 36 in FIG. 3B. It will be appreciated that rotation may be continued until a full cylindrical tissue removal volume is achieved. As a further alternative, it will be appreciated that the speed of rotation of shaft 12 may be increased relative to the speed of reciprocation so that the cylinder is formed as a series of circular or disc-shaped removal volumes which are in turn "stacked" over one another as the shaft is axially advanced in one direction only (the element 18 would cut through the tissue in a "propeller-like" fashion).

Figure 4:
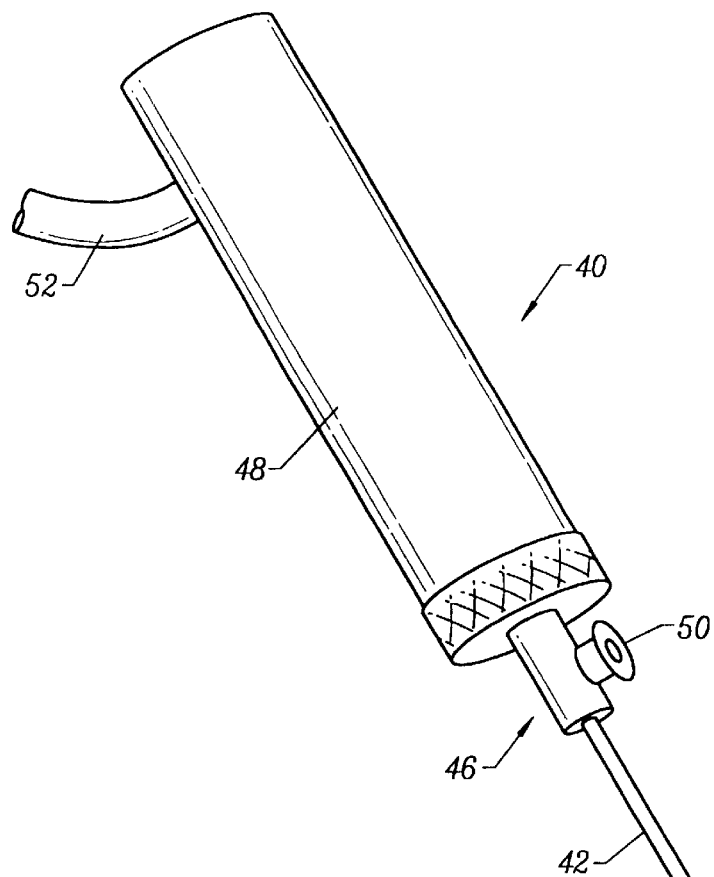
FIG. 4 illustrates a second apparatus constructed in accordance with the principles of the present invention.
Figure 5:
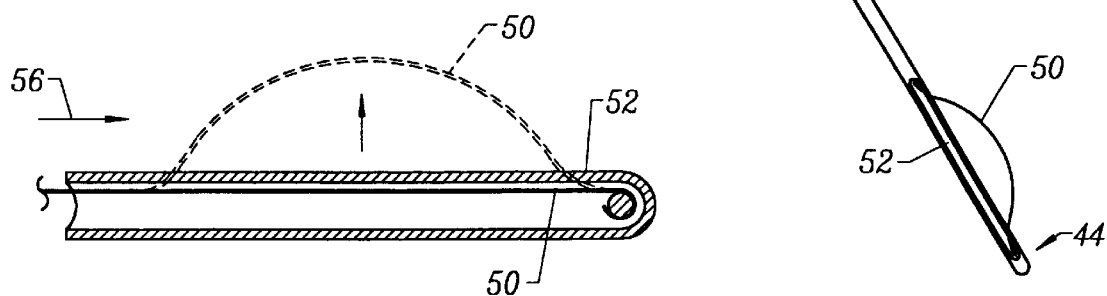
FIG. 5 is a detailed view of the distal end of the apparatus of FIG. 1, shown in section.

Referring now to FIGS. 4 and 5, a second embodiment of the tissue ablation device of the present invention will be described. Tissue ablation device 40 comprises a shaft 42 having a distal end 44 and proximal end 46. A handle 48 is attached to the proximal end of the shaft 46, and an aspiration connector 50 and power supply connector 52, are further provided, generally as described in connection with the first tissue ablation device 10.

An energy conductive element 50 provided in device 40, however, differs from that described with respect to device 10. In particular, a flexible energy conductive device 50, typically in the form of an elastic wire, is provided so that it can emerge radially outwardly from a slot 52 formed near the distal end 44 of the shaft 42. The wire 50 may be bowed outwardly by advancing a proximal portion of the wire 50 in a distal direction, as shown by arrow 56. It will be appreciated that the wire will assume an arcuate configuration, and that the degree to which the arc extends radially outward from the shaft will depend on how far the proximal end has been distally advanced. The wire 50 will be coupled to a suitable energy source through power supply connector 52, typically to a radiofrequency power supply.

Figure 6A:
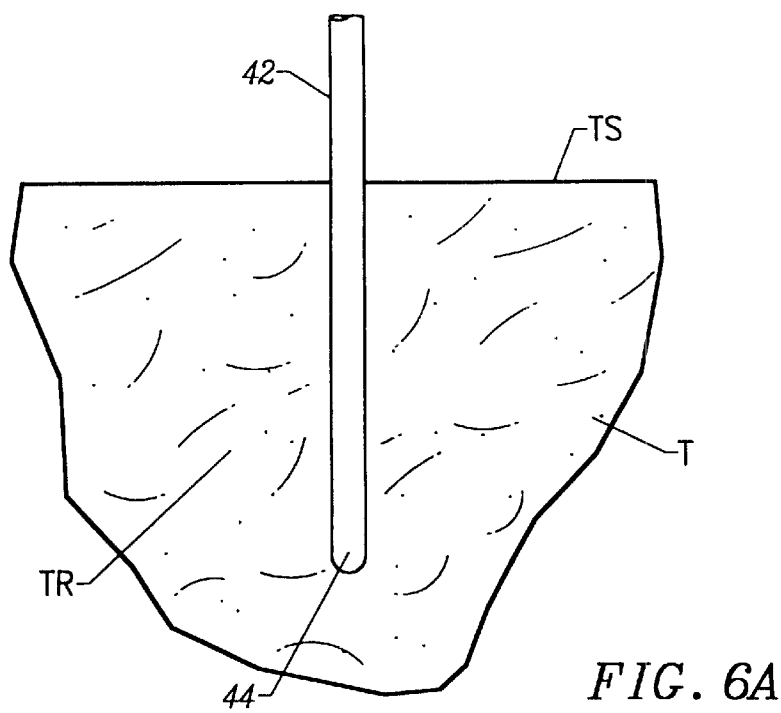
FIGS. 6A–6D illustrate use of the apparatus of FIGS. 4 and 5 in performing a method in accordance with the principles of the present invention.
Figure 6B:
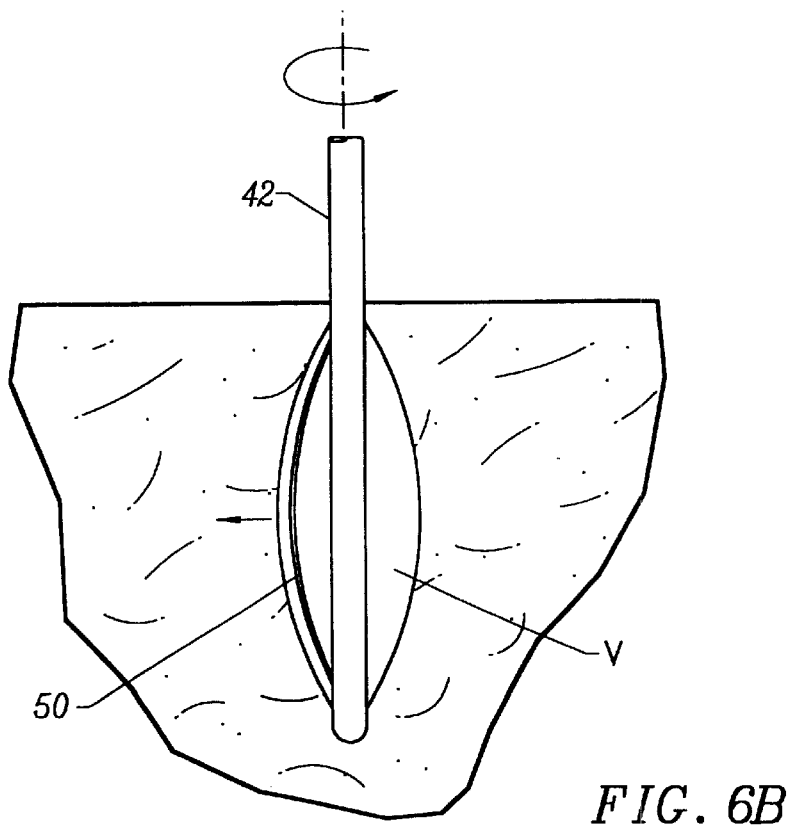
Figure 6C:
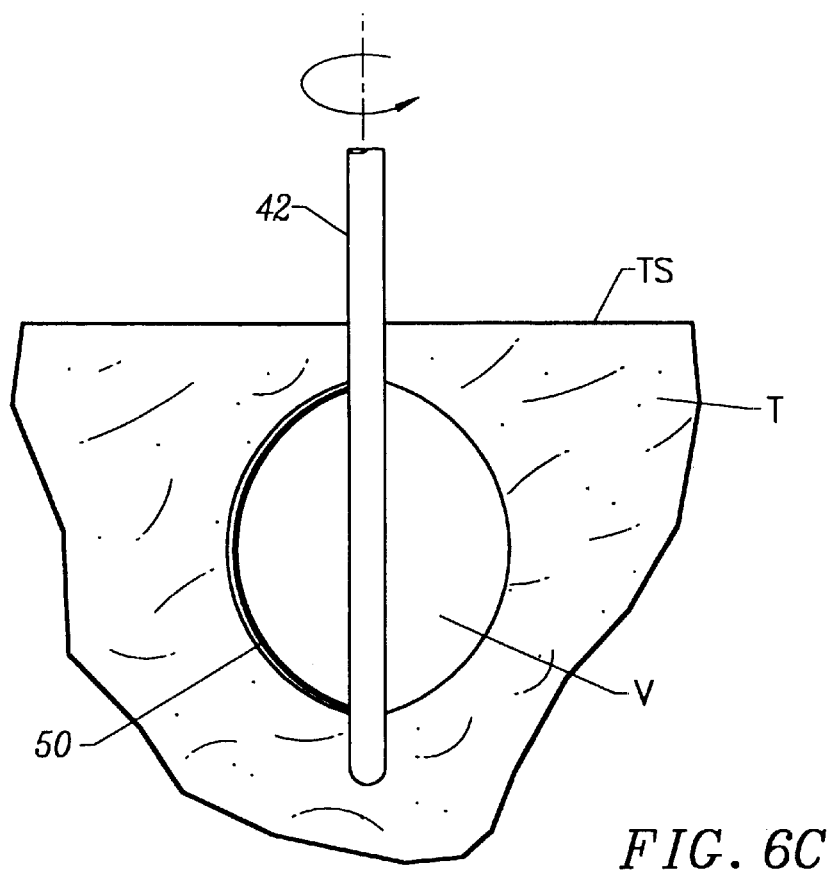
Figure 6D:
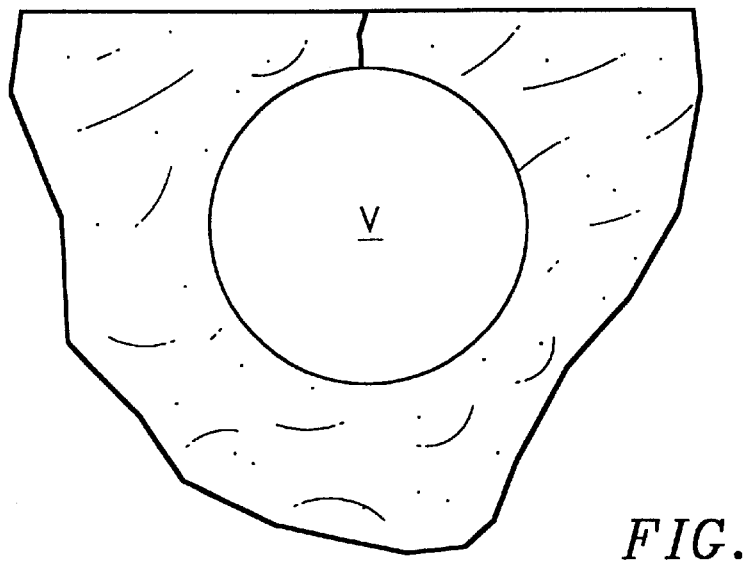

Use of the device 40 is illustrated in FIGS. 6A–6D. Device 10 is initially introduced so that distal end 44 of shaft 42 lies at or near a target region TR in tissue T beneath tissue surface TS. Treatment then commences by energizing the wire 50, advancing the wire 50 radially outward, as shown by the arrow in FIG. 6B, and rotating the shaft 42 as shown by the second arrow in FIG. 6B. It will be appreciated that the wire moves outwardly in a generally spiral pattern as the shaft is rotated and successively removes layers of the tissue to form a void V having a generally ovoid pattern, shown at its initial stages in FIG. 6B. As the wire 50 advances further outwardly, the ovoid shape of a void V becomes closer to spherical, as shown in FIG. 6C. At the end of the treatment, the void V will typically have a full spherical configuration, as shown in FIG. 6D. It would be possible, of course, to still further advance the wire 50 so that the void becomes increasingly large in its lateral dimension, thus becoming a flattened sphere. The ability to further extend the sphere, however, may be limited by the mechanical characteristics of the element 50 being rotated. The inner surface of void V will be cauterized in order to control bleeding, generally as described above in connection with the use of device 10. Moreover, the void V can optionally be filled with collagen, gelatin, or other tissue-filling materials, also as generally described above in connection with the first embodiment.

Figure 7A:
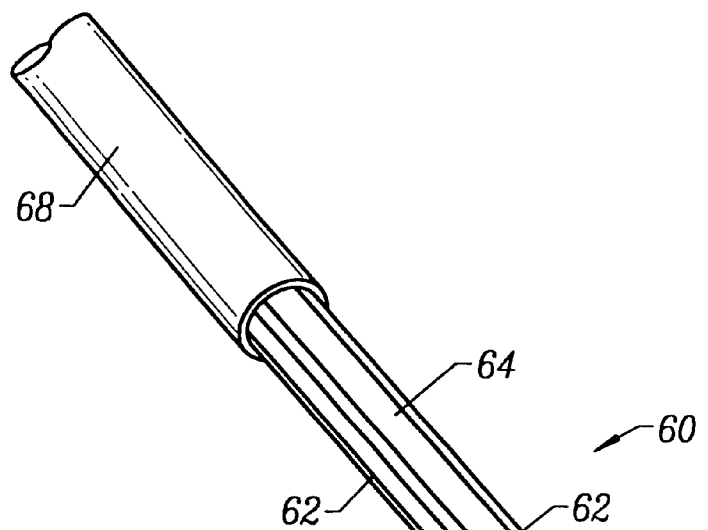
FIGS. 7A and 7B illustrate a third alternative construction for apparatus in accordance with the principles of the present invention.
Figure 7B:
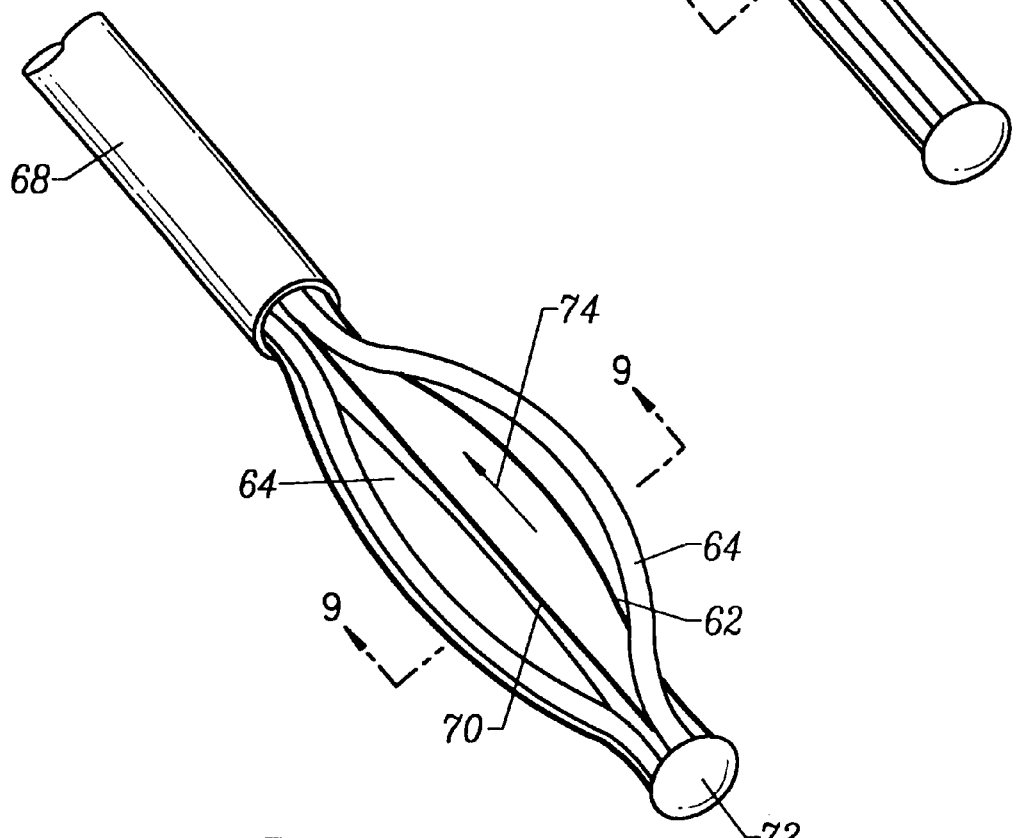
Figure 8:
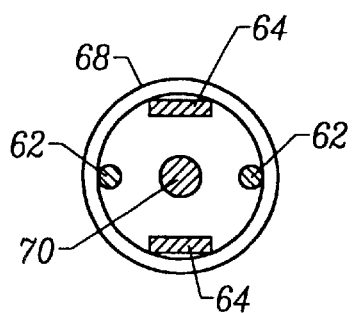
FIG. 8 is a cross-sectional view taken along line 8—8 of FIG. 7A.
Figure 9A:
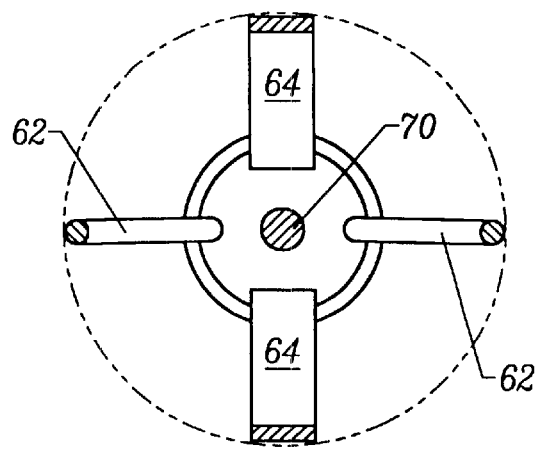
FIGS. 9A and 9B are alternative cross-sectional views taken along line 9—9 of FIG. 7B.
Figure 9B:
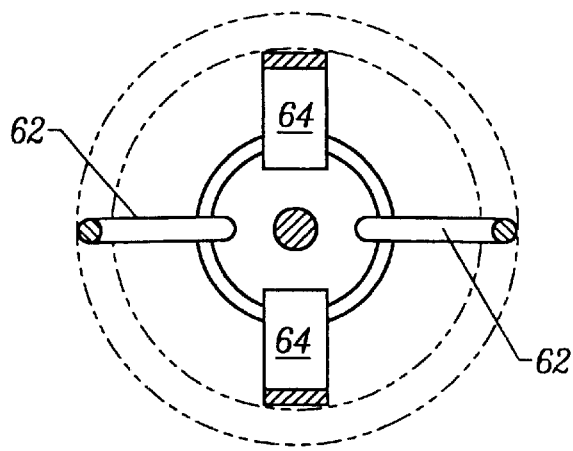

Referring now to FIGS. 7A and 7B, a further alternative embodiment for an energy conductive element array for use in devices constructed in accordance with the principles of the present invention will be described. Conductive element array 60 comprises a pair of diametrically opposed wire electrodes 62 and a pair of diametrically opposed ribbon electrodes 64. The electrodes 62 and 64 are attached to a distal end of shaft 68, and a central pull wire 70 is attached to a distal tip 72. By proximally advancing the pull bar 70 in the direction of arrow 74 (FIG. 7B), the tip 72 is drawn proximally, axially compressing the electrodes 62 and 64, causing them to expand radially outwardly. (The relationship between the electrodes 62 and 64 and the pull wire 70 is best shown in FIG. 8.) Usually, the wire electrodes 62 and ribbon electrodes 64 will advance radially outwardly at the same rate so that they lie at the same radial distance from the shaft 68, as illustrated in FIG. 9. In some instances, however, it will be desirable to have the wire electrodes 62 advance ahead of the ribbon electrodes 64, as illustrated in FIG. 9B. This will be a particular advantage when the device is driven in a bipolar fashion, with wires 62 driven at an opposite polarity from ribbon 64. Since the ribbons have a substantially greater surface area, they will act dispersive electrodes, while the wire electrodes 62 act as the cutting electrodes. By having the outer surfaces of the ribbon electrodes "trailing" the radially advancing wire electrodes 62, the ribbon electrodes can better act to cauterize the tissue surface which is being created.

Figure 10:
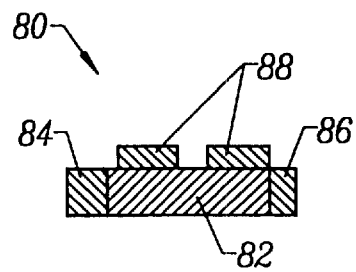
FIG. 10 illustrates an alternative construction for a ribbon electrode according to the principles of the present invention.

Ribbon electrodes can also be used by themselves, either singularly or in multiplies, in the devices and methods of the present application. In particular, a ribbon electrode having the cross-sectional configuration shown in FIG. 10 could be used for both cutting and cauterization in a bowed electrode device. Ribbon electrode 80 would have an electrically non-conductive core 82 and electrically connective cutting surfaces 84 and 86 formed on the leading edges thereof. One or more cauterizing electrodes 88 would be formed on either or both of the major surfaces of the core 82. This way, the electrode 80 could be driven so that either of the surfaces 84 and 86 initially engage tissue with radiofrequency energy having a cutting waveform. Simultaneously, or on a subsequent passage of the electrode 80, radiofrequency energy having a coagulation waveform could be applied to the newly created tissue surface using the electrode surfaces 88.

Figure 11:
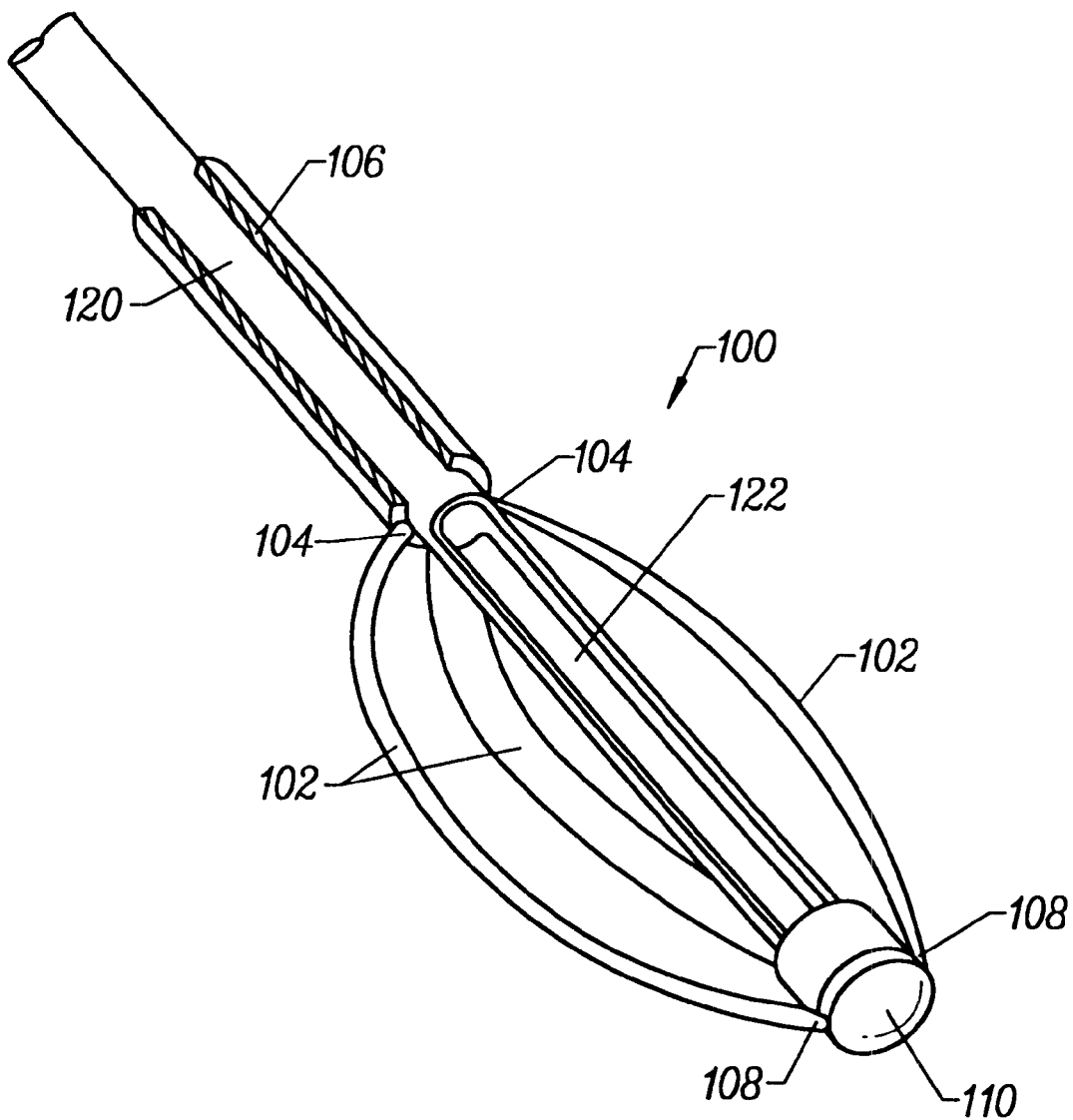
FIG. 11 illustrates a fourth alternative embodiment of the apparatus of the present invention.

A further embodiment of an energy conductive element array 100 constructed in accordance with the principles of the present invention is illustrated in FIG. 11. The array includes a plurality of ribbon electrodes 102, optionally being in the form of electrodes 80 (FIG. 10), which are connected at their proximal ends 104 to the distal end of the outer shaft 106. The distal ends 108 of the elements 102, in turn, are connected to an end cap 110 secured at the distal end of an inner shaft 120. The inner shaft 120 has a lumen which opens into an open chamber 122 formed in the distal end of the shaft 120. The opening 122 is suitable for collecting the vapor and cellular debris which is released during the tissue vaporization methods described herein. The elements 102 may be radially expanded and contracted by axially reciprocating the inner shaft 120 with respect to the outer shaft 106. The embodiment of FIG. 11 could be further modified to include only a single wire electrode and three ribbon electrodes (not shown). During cutting, the wire electrode could be powered and the three ribbon electrodes act as passive electrodes. During a subsequent coagulation step, the cutting wire electrode could be de-energized, the coagulation power applied to one of three ribbons, with the other two ribbons acting as passive electrodes. In order to enhance performance, the ribbon electrode through which the coagulation power is applied could have a smaller area than the two passive ribbon electrodes.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A tissue ablation device comprising:
   a shaft having a proximal end, a distal end, and a lumen therethrough,
   a substantially rigid energy conductive straight cylindrical pin attached to pivot about a fixed point on the shaft near its distal end;
   means for causing the element to pivot relative to the shaft;
   an aspiration connector coupled to the lumen near the proximal end of the shaft; and
   a power supply connector disposed near the proximal end of the shaft and electrically coupled to the energy conductive element.

2. A device as in claim 1, wherein the shaft is substantially rigid.

3. A device as in claim 1 or 2, wherein the shaft has a diameter in the range from 0.1 mm to 20 mm and a length in the range from 0.5 cm to 50 cm.

4. A device as in claim 1, wherein the shaft has a diameter in the range from 0.1 mm to 20 mm and a length in the range from 0.5 cm to 50 cm.

5. A device as in claim 1, further comprising a handle secured to the proximal end of the shaft.

6. A device as in claim 1, wherein the aspiration connector and the power supply connector are disposed on the handle.

7. A device as in claim 1, further comprising a motor attachable to the proximal end of the shaft.

8. A device as in claim 7, wherein the motor is attached to both rotate the shaft and move the substantially rigid energy conductive straight cylindrical pin relative to the shaft.

9. A device as in claim 1, wherein the substantially rigid energy conductive straight cylindrical pin comprises an electrode which conducts high frequency electrical energy.

10. A device as in claim 1, wherein the substantially rigid energy conductive straight cylindrical pin comprises a heating element.

11. A device as in claim 10, wherein the heating element comprises an optical fiber for delivering light energy to heat the energy conductive element.

12. A device as in claim 10, wherein the heating element comprises an electrical resistance heater.

13. A device as in claim 1, wherein the substantially rigid energy conductive straight cylindrical pin has a length in the range from 15 mm to 75 mm and a width in the range from 1 mm to 5 mm.

14. A device as in claim 13, wherein the substantially rigid energy conductive straight cylindrical pin is pivotally attached near its middle to the shaft.

15. A device as in claim 1, wherein the substantially rigid energy conductive straight cylindrical pin is pivotally attached near one end thereof to the shaft.

* * * * *